United States Patent
Sarbassov et al.

(10) Patent No.: US 12,310,986 B2
(45) Date of Patent: May 27, 2025

(54) COMPOSITIONS AND METHODS FOR THE TREATMENT OF CANCER CELLS BY INDUCTION OF CYTOTOXIC OXIDATIVE STRESS

(71) Applicant: Board of Regents, The University of Texas System, Austin, TX (US)

(72) Inventors: Dos D. Sarbassov, Houston, TX (US); Xinggang Wu, Houston, TX (US); Lee Ellis, Houston, TX (US); Rajat Bhattacharya, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 810 days.

(21) Appl. No.: 17/269,497

(22) PCT Filed: Aug. 20, 2019

(86) PCT No.: PCT/US2019/047334
§ 371 (c)(1),
(2) Date: Feb. 18, 2021

(87) PCT Pub. No.: WO2020/041364
PCT Pub. Date: Feb. 27, 2020

(65) Prior Publication Data
US 2021/0196753 A1    Jul. 1, 2021

Related U.S. Application Data

(60) Provisional application No. 62/720,257, filed on Aug. 21, 2018.

(51) Int. Cl.
*A61K 33/36*  (2006.01)
*A61K 31/375*  (2006.01)
*A61P 35/00*  (2006.01)

(52) U.S. Cl.
CPC ............ *A61K 33/36* (2013.01); *A61K 31/375* (2013.01); *A61P 35/00* (2018.01)

(58) Field of Classification Search
None
See application file for complete search history.

(56) References Cited

U.S. PATENT DOCUMENTS 9,931,315 B2   4/2018   Piazza et al.

FOREIGN PATENT DOCUMENTS

| EP | 3181118 | 6/2017 | |
|---|---|---|---|
| WO | WO 2016/069458 | 5/2016 | |
| WO | WO-2016069458 A1 * | 5/2016 | ........... A61K 31/122 |
| WO | WO 2017/100162 | 6/2017 | |

OTHER PUBLICATIONS

Yun, J., et al., Vitamin C selectively kills KRAS and BRAF mutant colorectal cancer cells by targeting GAPDH, Science, vol. 350 p. 1391 (2015) (Year: 2015).*
Hunter, J.C., et al., Biochemical and Structural Analysis of Common Cancer-Associated KRAS Mutations, Oncogenes and Tumor Suppressors, Sep. 1, 2015 (Year: 2015).*
Dinnen, R.D., et al., Redirecting apoptosis to aponecrosis induces selective cytotoxicity to pancreatic cancer cells through increased ROS, decline in ATP levels, and VDAC, Mol. Cancer Ther. 12(12), 2792-2803 (2013) (Year: 2013).*
Bachleitner-Hofmann, T., et al., Arsenic trioxide and ascorbic acid: synergy with potential implications for the treatment of acute myeloid leukaemia?, British Journal of Haematology, 2001, 112, 783-86 (Year: 2001).*
Roomi, M.W., et al., Growth suppression of malignant leukemia cell line in vitro by ascorbic acid (vitamin C) and its derivatives, Cancer Letters 122 (1998) 93-99 (Year: 1998).*
Zambrano, A., et al., Glut 1 in Cancer Cells and the Inhibitory Action of Resveratrol as A Potential Therapeutic Strategy, Int J Mol Sci. Jul. 2019; 20(13): 3374 (Year: 2019).*
Chang et al., "Phase II study of arsenic trioxide and ascorbic acid for relapsed or refractory lymphoid malignancies: a Wisconsin Oncology Network study," *Hematol Oncol.*, 27:11-16, 2009.
Di Biase et al., "Fasting-mimicking diet reduces HO-1 to promote T cell-mediated tumor cytotoxicity," *Cancer Cell*, 30:136-146, 2016.
Dinnen et al., "Redirecting apoptosis to aponecrosis induces selective cytotoxicity to pancreatic cancer cells through increased ROS, decline in ATP levels, and VDAC," *Mol Cancer Ther.*, 12(12):2792-2803, 2013.
Extended European Search Report issued in European Application No. 19851608.0, mailed Apr. 13, 2022.
Grad et al., "Ascorbic acid enhances arsenic trioxide-induced cytotoxicity in multiple myeloma cells," *Blood*, 98:805-813, 2001.
Li, "Vitamin C, a multi-tasking molecule, finds a molecular target in killing cancer cells," *Reactive Oxygen Species*, 1:141-156, 2016.
Noguera et al., "High-dose ascorbate and arsenic trioxide selectively kill acute myeloid leukemia and acute promyelocytic leukemia blasts *in vitro,*" *Oncotarget*, 8(20):32550-32565, 2017.
Office Action issued in Eurasian Application No. 202190580/28, mailed Jun. 28, 2022.
PCT International Preliminary Report on Patentability issued in International Application No. PCT/US2019/047334, mailed Mar. 4, 2021.
PCT International Search Report and Written Opinion issued in International Application No. PCT/US2019/047334, mailed Nov. 12, 2019.
Prasad et al., "Sodium ascorbate potentiates the growth inhibitory effect of certain agents on neuroblastoma cells in culture," *Proc. Natl. Acad. Sci. USA*, 76(2):829-832, 1979.

(Continued)

*Primary Examiner* — H. Sarah Park
(74) *Attorney, Agent, or Firm* — Parker Highlander PLLC

(57) ABSTRACT

Provided herein are methods and compositions for the treatment of cancers with D-VC and arsenic trioxide. In some aspects, cancers for treatment according to the embodiments include cancers with increased GLUT1 expression and/or comprise KRAS mutation.

8 Claims, 9 Drawing Sheets

(56) References Cited

OTHER PUBLICATIONS

Roomi et al., "Growth suppression of malignant leukemia cell line in vitro by ascorbic acid (vitamin C) and its derivatives," *Cancer Letters*, 122:93-99, 1998.

Yedjou et al., "Ascorbic acid potentiation of arsenic trioxide anticancer activity against acute promyelocytic leukemia," *Arch Drug Info*, 2:59-65, 2009.

Yun et al., "Vitamin C selectively kills *KRAS* and *BRAF* mutant colorectal cancer cells by targeting GAPDH," *Science*, 350(6266):1391-1396, 2015.

Begimbetova et al., "The Vitamin C Enantiomers Possess a Comparable Potency in the Induction of Oxidative Stress in Cancer Cells but Differ in Their Toxicity," Int J Mol Sci, 25:2531, 2024, pp. 1-14.

Begimbetova et al., "The Oxidative Drug Combination for Suppressing KRAS G12D Inducible Tumour Growth," Biomed Res Int, 2022:9426623, 2022, pp. 1-14.

Burska et al., "Enhancing an Oxidative "Trojan Horse" Action of Vitamin C with Arsenic Trioxide for Effective Suppression of KRAS-Mutant Cancers: a Promising Path at the Bedside," Cells, 11:3454, 2022, pp. 1-25.

\* cited by examiner

COMPOSITIONS AND METHODS FOR THE TREATMENT OF CANCER CELLS BY INDUCTION OF CYTOTOXIC OXIDATIVE STRESS

This application is a national phase application under 35 U.S.C. § 371 of International Application No. PCT/US2019/047334, filed Aug. 20, 2019, which claims the benefit of U.S. Provisional Patent Application No. 62/720,257, filed Aug. 21, 2018, the entirety of each of which is incorporated herein by reference.

BACKGROUND OF THE INVENTION

1. Field of the Invention

The present invention relates generally to the field of oncology. More particularly, it concerns treatment of cancer by the induction of a cytotoxic oxidative stress.

2. Description of Related Art

Many metastatic cancers are currently incurable, and 5-year survival rates are still very low, despite decades of research and ever growing funding. For example, KRAS mutations are common in the pancreatic, colorectal, and lung cancers, and there is presently no effective intervention for the KRAS oncogene. One possible approach to treating cancers, such as KRAS mutant cancers, is to induce oxidative stress, which can selectively kill cancer cells relative to surrounding normal tissue. However, to date, there remains a need for methods and compositions that are capable of inducing sufficient oxidative stress that is selective for cancer cells to provide therapeutic efficacy.

SUMMARY OF THE INVENTION

In a first embodiment, there is provided a method for treating cancer in a subject comprising subjecting the cancer cells to oxidative stress and administering an effective amount of D-VC or pharmaceutically acceptable salts thereof to the subject. In some aspects, subjecting the cancer cells to oxidative stress comprises administering an effective amount of an oxidizing agent to the subject. For example, in some aspects, the oxidizing agent is selected from the group consisting of (without limitation) arsenic trioxide (ATO), a methyl ester of 2-cyano-3,12-dioxo-oleana-1,9-dien-28-oic acid (CDDO-Me), curcumin, betulinic acid, a synthetic nonsteroidal anti-inflammatory drug (NSAID), GT-094, celastrol, tolperisone and lanperisone (a tolperisone derivative).

In some embodiments, the present disclosure provides methods for treating cancer comprising administering to a subject in need thereof a therapeutically effective dose of arsenic trioxide (ATO) and D-vitamin C (D-VC also known as D-Ascorbic Acid) or pharmaceutically acceptable salts thereof. In some aspects, the cancer is a KRAS mutant cancer. In some aspects, the cancer has been tested and determined to comprise a KRAS mutation. In some aspects, the cancer exhibits elevated GLUT1 expression. In some aspects, the cancer has been tested and determined to exhibit elevated GLUT1 expression or show a high glucose absorbance. In some aspects, the cancer is a KRAS mutant cancer and exhibits elevated GLUT1 expression.

In certain aspects, the oxidative stress is applied separately from the D-VC administration. In further aspects, the oxidative stress is applied within 24 hours of D-VC administration. In still further aspects, the oxidative stress is applied within 8, 6, 4, or 2 hours of D-VC administration. In still further aspects, the oxidative stress is applied within 1 hour of D-VC administration. In some aspects, the oxidative stress is applied at essentially the same time that D-VC is administered. In other aspects, the D-VC is administered subsequently to the oxidative stress being applied. In further aspects, the D-VC is administered about 2 hours following oxidative stress being applied.

In some aspects, the oxidizing agent, e.g., ATO, and D-VC are administered in separate compositions. In further aspects, the oxidizing agent, such as ATO, and D-VC are administered within 24 hours of each other. In still further aspects, the oxidizing agent (e.g., ATO) and D-VC are administered within 8, 6, 4, or 2 hours of each other. In still further aspects, the oxidizing agent (e.g., ATO) and D-VC are administered within 1 hour of each other. In some aspects, the ATO and D-VC are co-administered. In other aspects, the D-VC is administered subsequently to the oxidizing agent (e.g., ATO). In further aspects, the D-VC is administered about 2 hours following administration of the oxidizing agent (e.g., ATO).

In some aspects, the subject is fasting in some aspects, the subject has been fasting for at least 1 hour prior to the administration of the D-VC. In other aspects, the subject has been fasting for at least 2, 4, 6, 8, 10, 12, 18 or 24 hours prior to the administration of the D-VC. In some aspects, the methods further comprise testing the blood glucose level of the subject before administration of the D-VC. In some aspects, the oxidizing agent (e.g., ATO) and D-VC are formulated in the same composition. In some aspects, the oxidizing agent (e.g., ATO) and D-VC are administered at least 2, 3, 4, 5, 6, 7, 8, 9, 10, 11, 12, 13, 14, or 15 times. In some aspects, the oxidizing agent (e.g., ATO) and D-VC are administered daily for a period of one week, two weeks, one month two months or three months. In some aspects, the oxidizing agent is ATO and is administered at a dose of between about 10 µg/kg to about 10 mg/kg. In further aspects, the ATO is administered at a dose of between about 100 µg/kg to about 50 mg/kg. In further aspects, the ATO is administered at a dose of between about 0.1 mg/kg to about 5 mg/kg. For example, the ATO can be administered at a dose of at least 0.1 mg/kg to about 0.5, 1, 2, 3, or 4 mg/kg. In still further aspects, the ATO is administered at a dose of about 0.2 mg/kg.

In some aspects, the D-VC is administered at a dose of between about 5 mg/kg to about 30 g/kg. In further aspects, the D-VC is administered at a dose of between about 15 mg/kg to about 20 g/kg. In further aspects, the D-VC is administered at a dose of between about 150 mg/kg to about 15 g/kg. In still further aspects, the D-VC is administered at a dose of about 1.5 g/kg. In some aspects, the subject is fasting during the administration of the oxidizing agent (e.g., ATO) and D-VC. In some aspects, the subject has been fasting for at least 2 hours prior to the administration of the oxidizing agent (e.g., ATO) and D-VC. In some aspects, the subject continues to fast for at least 2 hours following the administration of oxidizing agent (e.g., ATO) and D-VC.

In some aspects, the cancer is leukemia, colorectal cancer, pancreatic cancer or lung cancer. In further aspects, the leukemia is acute promyelocytic leukaemia (APL). In some aspects, the cancer is a pancreatic, colorectal cancer or multiple myeloma. In some aspects, the cancer comprises a KRAS mutation and/or exhibits elevated. GLUT1 expression. In some aspects, the ATO and/or D-VC are administered intravenously, intraperitoneally, intratracheally, intratumorally, intramuscularly, endoscopically, intralesionally, percutaneously, subcutaneously, regionally, or by direct injection or perfusion. In other aspects, the ATO and/or D-VC are administered by a non-parenteral route. In further aspects, the ATO and/or D-VC are administered by a topical, epidermal or mucosal route. In some aspects, the ATO and D-VC are administered intranasally, orally, vaginally, rectally, sublingually, or topically. In some aspects, the ATO and D-VC are administered by the same route of administration. In some aspects, the methods further comprise treatment with at least one other anti-cancer therapy. In further aspects, the at least one other anti-cancer therapy is selected from tumor resection, chemotherapy, immunotherapy, and radiotherapy. In further aspects, the at least one other anti-cancer therapy comprises an oxidizing agent. In particular aspects, the oxidizing agent is selected from the group consisting of a methyl ester of 2-cyano-3,12-dioxo-oleana-1,9-dien-28-oic acid (CDDO-Me), curcumin, betulinic acid, a synthetic nonsteroidal anti-inflammatory drug (NSAID), GT-094, celastrol, tolperisone and lanperisone In further embodiments, the present disclosure provides pharmaceutical compositions comprising an oxidizing agent (e.g., arsenic trioxide (ATO), a methyl ester of 2-cyano-3, 12-dioxo-oleana-1,9-dien-28-oic acid (CDDO-Me), curcumin, betulinic acid, a synthetic nonsteroidal anti-inflammatory drug (NSAID), GT-094, celastrol, tolperisone and lanperisone (a tolperisone derivative)) and D-VC, or pharmaceutically acceptable salts thereof, formulated in a pharmaceutically acceptable excipient. In still further embodiments, the present disclosure provides pharmaceutical compositions comprising arsenic trioxide (ATO) and D-VC, or pharmaceutically acceptable salts thereof, formulated in a pharmaceutically acceptable excipient.

In still other embodiments, the present disclosure provides methods for identifying a subject for treatment with an oxidizing agent (e.g., ATO) and D-VC therapy comprising testing a sample from the subject to determine if the subject has a cancer that comprises a KRAS mutation and/or exhibits elevated GLUT1 expression, wherein if the cancer comprises a KRAS mutation and/or exhibits elevated GLUT1 expression or a high glucose absorption then the subject is a candidate for therapy with a ATO and D-VC therapy. In some aspects, the methods further comprise administering ATO and D-VC therapy to the identified subject.

In some embodiments, the present disclosure provides methods for treating cancer in a subject comprising subjecting the cancer cells to oxidative stress by administering an effective amount of arsenic trioxide (ATO) or pharmaceutically acceptable salts thereof and an effective amount of a second oxidizing agent to the subject. In some aspects, the second oxidizing agent is selected from the group consisting of a methyl ester of 2-cyano-3,12-dioxo-oleana-1,9-dien-28-oic acid (CDDO-Me), curcumin, betulinic acid, a synthetic nonsteroidal anti-inflammatory drug (NSAID), GT-094, celastrol, tolperisone and lanperisone. In some aspects, the cancer is a KRAS mutant cancer. In some aspects, the cancer has been tested and determined to comprise a KRAS mutation. In some aspects, the cancer exhibits elevated GLUT1 expression or a high glucose absorbance. In some aspects, the cancer has been tested and determined to exhibit elevated GLUT1 expression. In some aspects, the cancer is a KRAS mutant cancer and exhibits elevated GLUT1 expression. In some aspects, the second oxidizing agent is administered within 24 hours of ATO administration. In some aspects, the second oxidizing agent is administered within 8, 6, 4, or 2 of ATO administration. In some aspects, the second oxidizing agent is administered within 1 hour of ATO administration. In some aspects, the ATO is administered after the second oxidizing agent is administered. In further aspects, the ATO is administered about 2 hours following the second oxidizing agent. In some aspects, the subject is fasting. In some aspects, the subject has been fasting for at least 1 hour prior to the administration of the ATO. In further aspects, the subject has been fasting for at least 2, 4, 6, 8, 10, 12, 18 or 24 hours prior to the administration of the ATO. In some aspects, the methods further comprise testing the blood glucose level of the subject before administration of the ATO.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6 xenograft tumors after 12 injections. Pictured are the xenograft tumors of each of the 5 mice per treatment condition as described in FIG. 6 after 12 injections (2 weeks of treatment). Scaring is observed in several tumors, including all of the D-VC+ATO treated tumors.

DESCRIPTION OF ILLUSTRATIVE EMBODIMENTS

Figure 1:
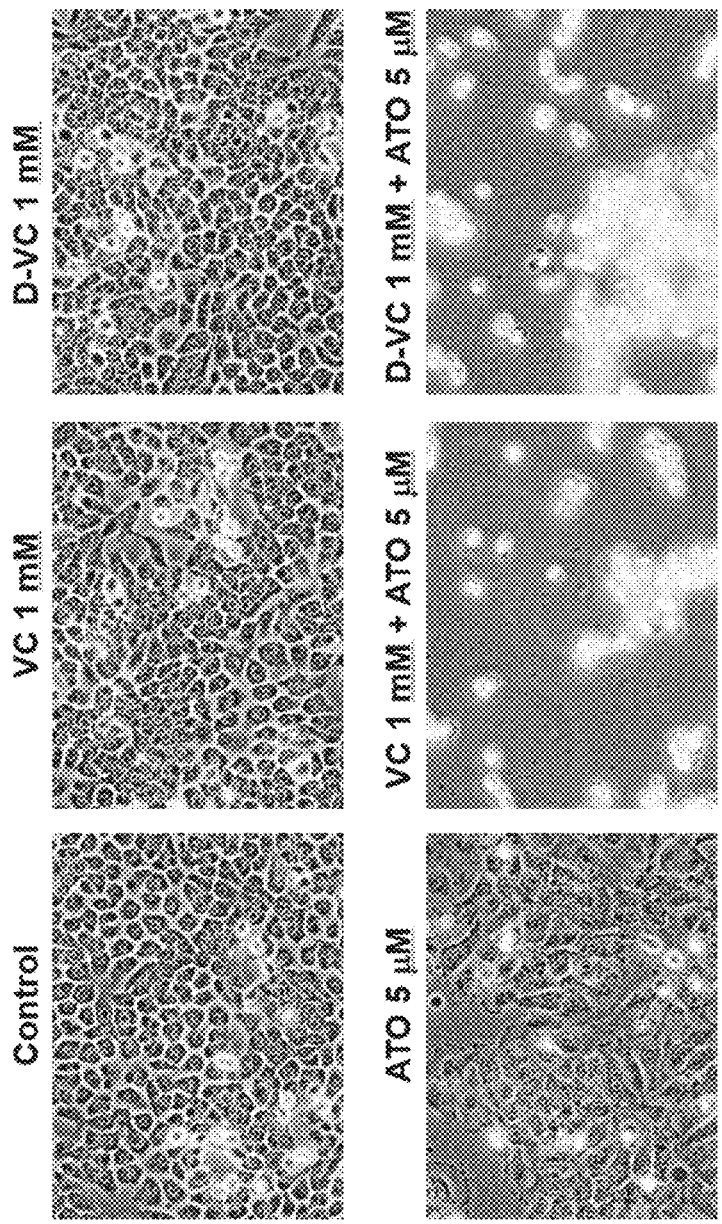
FIG. 1: Vitamin C/ATO and D-Vitamin C/ATO combination treatments are effective for inducing cytotoxicity in KRAS mutant cancer cells. Colorectal HCT116 cancer cells were treated with the indicated solutions for 72 hours: control (phosphate buffered saline, PBS, was added to the culture medium in 1:1000 dilution), VC 1 mM (Vitamin C was used at 1 mM concentration), D-VC 1 mM (D-Vitamin C was used at 1 mM concentration), ATO 5 μM (Arsenic Trioxide was used at 5 μM concentration) and the combination of VC 1 mM with ATO 5 μM or D-VC 1 mM with ATO 5 μM. The cell images are shown with the labeling indicating cell treatments.

Vitamin C in its natural form, also referred to herein as VC, L-VC, or its chemical name L-ascorbic acid, can induce oxidative stress in certain cancer cells, such as KRAS mutant cancers. Studies described herein demonstrate that the D enantiomer of vitamin C (D-VC), alone or in combination with and oxidizing agent such as arsenic trioxide, could induce significant oxidative stress cancer cells, such as KRAS mutant cancers. Specifically, the studies show that the optical isomer of vitamin C, D-vitamin C (also referred to herein as D-VC or D-ascorbic acid), is highly effective at inducing oxidative stress in KRAS mutant cancer cells. To strengthen the oxidative impact of D-VC on the KRAS mutant cells, D-VC was administered with another oxidizing compound, arsenic trioxide (ATO). The studies presented herein show that the D-VC/ATO combination is highly cytotoxic to the KRAS mutant cancer cells of both human and mouse origin. Further, the data provided herein indicate that the D-VC/ATO combination application is significantly more effective in suppressing KRAS mutant tumor growth in a mouse xenograft model than the combination of vitamin C and ATO. As KRAS mutations are common in pancreatic, colorectal, and lung cancers and there is presently no effective intervention of the KRAS oncogene at this time, the present disclosure provides a potent cytotoxic combination to specifically target the KRAS mutant cancer cells. Further, this combination of D-VC and ATO can be applied also to any type of cancer associated with a high expression of GLUT1.

Accordingly, in certain embodiments, the present disclosure provides compositions and methods for the treatment of cancer by treatment with arsenic trioxide and D-VC.

I. METHODS OF TREATMENT

In one aspect, provided herein are methods for treating cancer in a subject comprising administering to the subject a therapeutically effective amount of arsenic trioxide and D-VC.

Tumors for which the present treatment methods are useful include any malignant cell type, such as those found in a solid tumor or a hematological tumor. Particularly, the cancer may be a cancer overexpressing the GLUT1 transporter, such as a KRAS mutant cancer or cancers that show a high glucose absorbance.

Cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma. Exemplary cancers which may be treated using the methods of the present disclosure may overexpress GLUT1, such as KRAS mutant cancers.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; strum ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In certain embodiments, the therapeutically effective amount of the ATO and D-VC is administered to the subject intravenously, intratumorally, or intraperitoneally. The appropriate dosage of ATO and D-VC may be determined based on the type of cancer to be treated, the severity and course of the disease, the clinical condition of the individual, and the discretion of the attending physician.

A. Combination Therapies

In certain embodiments, the methods provided herein further comprise a step of administering at least one additional therapeutic agent to the subject. All additional therapeutic agents disclosed herein will be administered to a subject according to good clinical practice for each specific composition or therapy, taking into account any potential toxicity, likely side effects, and any other relevant factors.

In certain embodiments, the additional therapy may be immunotherapy, radiation therapy, surgery (e.g., surgical resection of a tumor), chemotherapy, bone marrow transplantation, or a combination of the foregoing. The additional therapy may be targeted therapy. In certain embodiments, the additional therapy is administered before the primary treatment (i.e., as adjuvant therapy). In certain embodiments, the additional therapy is administered after the primary treatment (i.e., as neoadjuvant therapy).

In certain embodiments, the additional therapeutic agent comprises treatment with radiotherapy. In certain embodiments, the radiotherapy is selected from the group consisting of gamma rays ($\gamma$-rays), X-rays, microwaves, proton beam irradiation, ultraviolet irradiation, and the directed delivery of radioisotopes to the tumor. In certain embodiments, the radiotherapy comprises treatment with X-rays. In certain embodiments, the X-rays are administered in daily doses of 50 to 200 roentgens over a period of three to four weeks. In certain embodiments, the X-rays are administered in a single dose of 2000 to 6000 roentgens. In certain embodiments, the radiotherapy comprises directed delivery of radioisotopes to the tumor. Dosage ranges for radioisotopes vary widely depending on the half-life of the isotope, the strength and type of radiation emitted, and the degree of uptake by tumor cells, but determination of an appropriate therapeutically effective dose is within the level of ordinary skill in the art.

In certain embodiments, the additional therapeutic agent comprises administration of agents for the treatment of side-effects associated with the primary treatment (e.g., nausea, cachexia, and the like). In certain embodiments, the additional therapy comprises an immunotherapy. In certain embodiments, the additional therapy comprises radiation therapy. In some embodiments, the radiotherapy comprises gamma irradiation. In certain embodiments, the additional therapy comprises surgery. In certain embodiments, the additional therapy comprises a combination of radiation therapy and surgery. In certain embodiments, the additional therapy comprises treatment with a class of chemotherapeutic agent selected from the group consisting of alkylating agents, anthracyclines, cytoskeletal disruptors, epothilones, histone deacetylase inhibitors, topoisomerase I inhibitors, topoisomerase II inhibitors, kinase inhibitors, nucleotide analogs and nucleotide precursor analogs, peptide antibiotics, platinum-based compounds, retinoids, vinca alkaloids and derivatives thereof.

The additional therapies contemplated herein may be administered before, after, or concurrently with administration of the compositions provided herein. In certain embodiments, the additional therapy is administered before the compositions provided herein. In certain embodiments, the additional therapy is administered after the compositions provided herein. In certain embodiments, the additional therapy is administered at one or more intervals before or after administration of the compositions provided herein. Determination of an appropriate interval for administration of an additional therapy such that the subject being treated benefits from the combination therapy is within the level of ordinary skill in the art.

In certain embodiments, the additional therapy is immune checkpoint inhibitor therapy. An immune checkpoint inhibitor inhibits an immune checkpoint protein selected from the group consisting of programmed cell death pathway 1 (PD-1/CD279) and its ligands (PD-L1/CD274 and PD-L2/CD273), cytotoxic T lymphocyte-associated antigen 4 (CTLA-4/CD152), lymphocyte-activation gene 3 (LAG-3/CD223), B and T lymphocyte attenuator (BTLA), T cell immunoreceptor with Ig and immunoreceptor tyrosine-based inhibitory motif (ITIM) domains (TIGIT), T cell immunoglobulin domain and mucin domain 3 (TIM-3/HAVcr2), killer immunoglobulin-like receptor (KIR/

CD158), V-domain immunoglobulin suppressor of T cell activation (VISTA), and the adenosine A2a receptor (A2aR).

The immune checkpoint inhibitors may be drugs such as small molecules, recombinant forms of ligand or receptors, or, in particular, are antibodies, such as human antibodies. Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In certain embodiments, the immune checkpoint inhibitor is a PD-1 binding antagonist. In certain embodiments, the PD-1 binding antagonist is an anti-PD-1 antibody. In certain embodiments, the anti-PD-1 antibody is selected from the group consisting of nivolumab, pembrolizumab, and CT-011. In certain embodiments, the PD-1 binding antagonist is an immunoadhesin (e.g., an immunoadhesin comprising an extracellular or PD-1 binding portion of PDL1 or PDL2 fused to an immunoglobulin constant region (e.g., an Fc region of an immunoglobulin sequence).

In certain embodiments, the immune checkpoint inhibitor is a CTLA-4 binding antagonist. In certain embodiments, the CTLA-4 binding antagonist is an anti-CTLA-4 antibody. In certain embodiments, the anti-CTLA-4 antibody is selected from the group consisting of ipilimumab and tremelimumab.

B. Pharmaceutical Compositions

In another aspect, provided herein are pharmaceutical compositions and formulations comprising arsenic trioxide (ATO), D-VC, and a pharmaceutically acceptable carrier.

Pharmaceutical compositions and formulations as described herein can be prepared by mixing the active ingredients (ATO and D-VC) having the desired degree of purity with one or more optional pharmaceutically acceptable carriers (Remington's Pharmaceutical Sciences 22$^{nd}$ edition, 2012), in the form of aqueous solutions, such as normal saline (e.g., 0.9%) and human serum albumin (e.g., 10%). Pharmaceutically acceptable carriers are generally nontoxic to recipients at the dosages and concentrations employed, and include, but are not limited to: buffers such as phosphate, citrate, and other organic acids; antioxidants; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zinc-protein complexes); and/or non-ionic surfactants such as polyethylene glycol (PEG).

II. KITS AND DIAGNOSTICS

In various aspects of the invention, a kit is envisioned containing diagnostic agents, therapeutic agents, and/or other therapeutic and delivery agents. In some embodiments, a kit for preparing and/or administering a therapy of the embodiments. The kit may comprise reagents capable of use in administering an active or effective agent(s). For example, reagents of the kit may include at least one pharmaceutical formulation of D-VC and at least one pharmaceutical formulation of ATO, as well as reagents to prepare, formulate, and/or administer the components of the embodiments. In further aspects, a kit may comprise diagnostic reagents, such as reagents for determining GLUT1 expression and/or KRAS status of a sample.

In some embodiments, the kit may also comprise a suitable container means, which is a container that will not react with components of the kit, such as an eppendorf tube, a syringe, a bottle, or a tube. The container may be made from sterilizable materials such as plastic or glass.

The kit may further include an instruction sheet that outlines the procedural steps of the methods, and will follow substantially the same procedures as described herein or are known to those of ordinary skill.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—In Vitro Study of D-VC Treatment of KRAS Mutant Cancer Cells

Colorectal HCT116 cancer cells were treated for 72 hours with PBS, a 1 mM Vitamin C (VC) solution, 1 mM D-Vitamin CVC (D-VC also referred as D-ascorbic acid), 5 µM arsenic trioxide (ATO), Vitamin C and ATO (VC/ATO), or D-VC and ATO (D-VC/ATO) (FIG. 1). As expected, ATO caused a mild cytotoxic impact compared to buffer alone, while treatment with Vitamin C and ATO induced much stronger cytotoxicity than buffer or vitamin C alone (FIG. 1). Interestingly, treatment with D-VC and ATO caused an equally robust cytotoxicity (FIG. 1). The similar synergistic cytotoxic effect of VC/ATO and D-VC/ATO has been also observed in other KRAS mutant cancer cells, including HPAC and MiaPaCA2 (pancreatic) and A549 (lung) cancer cells. However, neither combination induced cytotoxicity in PC3 (PTEN null prostate cancer cells) or primary human lung fibroblasts, indicating induction of cytotoxicity may be limited to KRAS mutant cancer cells.

Figure 2:
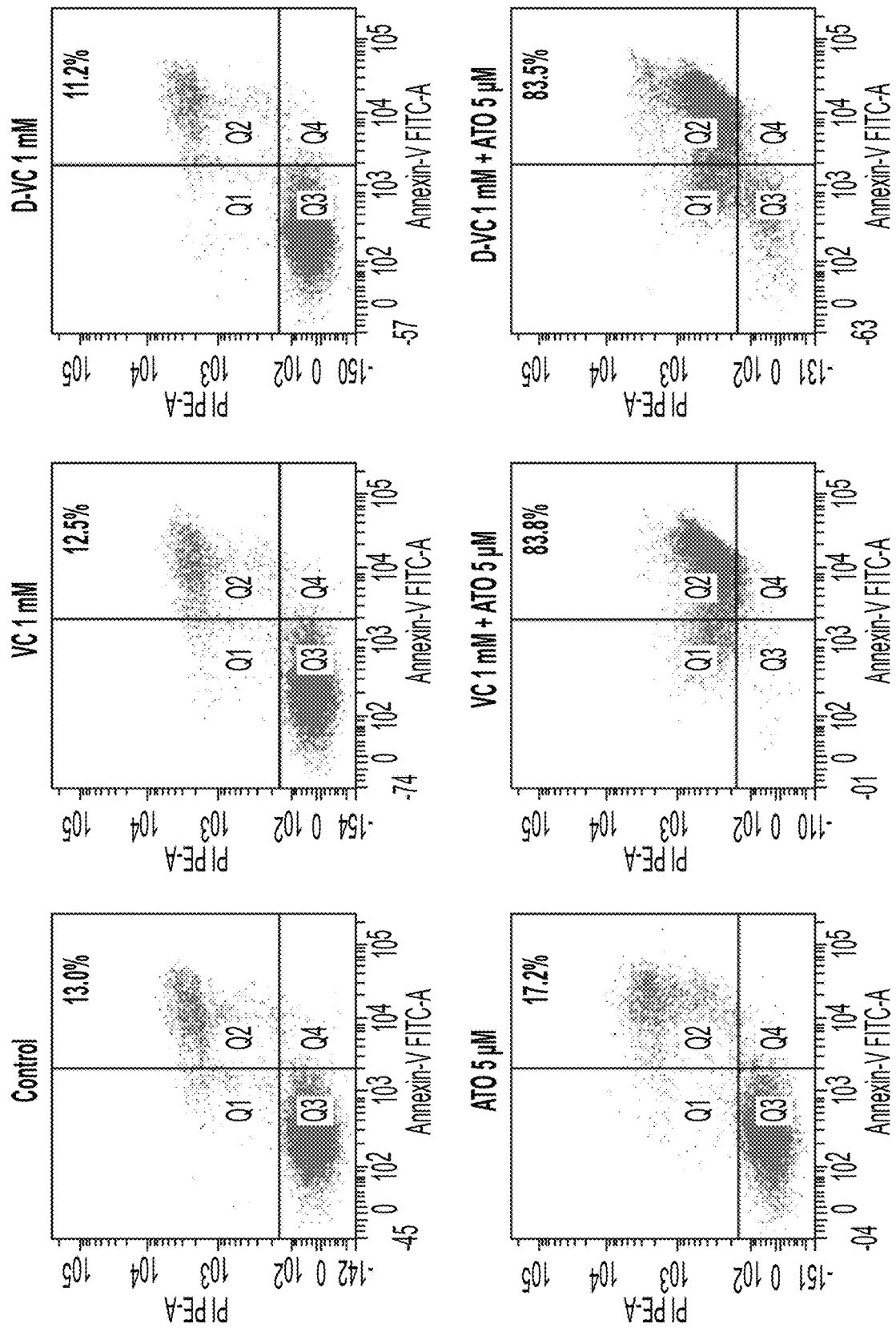
FIG. 2: Apoptotic flow cytometric analysis of HCT116 cancer following drug treatments. HCT116 cells were treated with the drugs as described in the FIG. 1 and following treatments the cells were stained with Annexin-V FITC and sorted.
Figure 3:
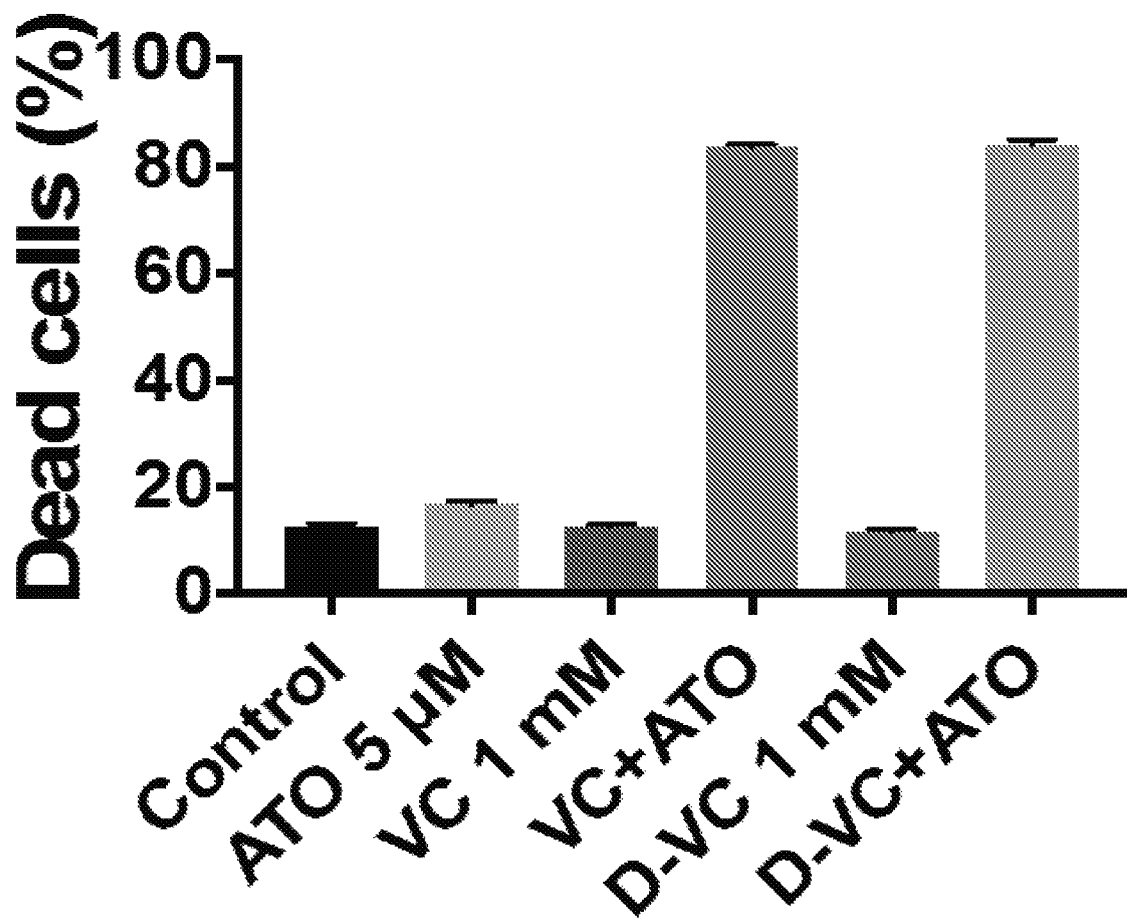
FIG. 3: Graphical representation of apoptosis by flow cytometry data. Apoptotic flow cytometric data shown in the FIG. 2 is presented as a graph.

To confirm these results, apoptosis was measured in a flow cytometric assay detecting Annexin V conjugated to FITC to measure apoptosis (FIG. 2). Treatment with Vitamin C, or its D enantiomer, showed a level of apoptosis similar to the buffer control (FIGS. 2 and 3, comparing VC and D-VC vs PBS). As expected, treatment with 5 µM ATO induced a low increase in apoptosis over the buffer control, but treatment with vitamin C or D-vitamin C along with ATO induced significantly greater apoptosis than ATO alone (FIGS. 2 and 3).

Figure 4:
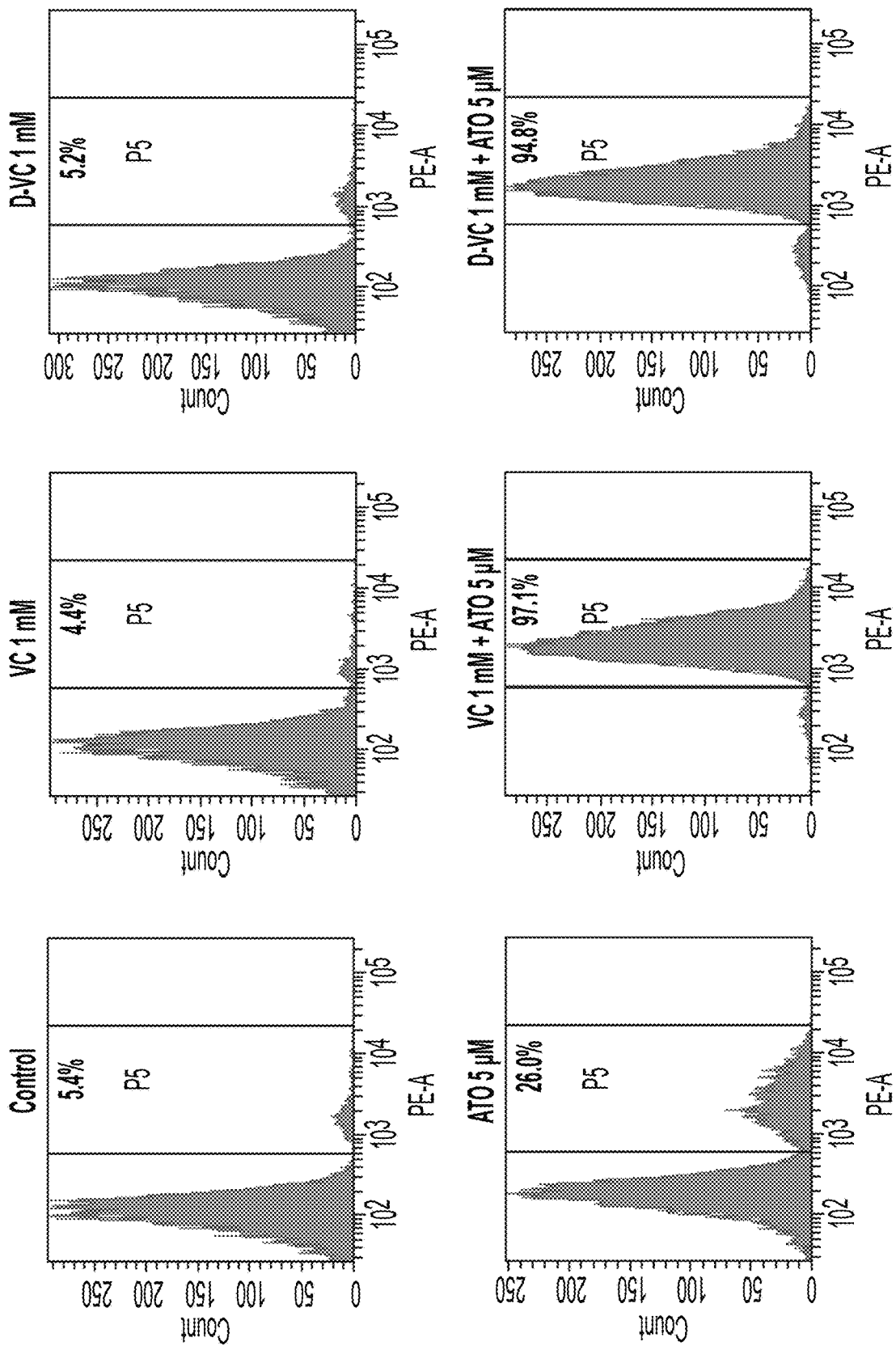
FIG. 4: Detection of reactive oxygen species (ROS) by flow cytometry. HCT116 cells were treated with the indicated compounds as described in the FIG. 1 and analyzed by flow cytometry to detect the presence of reactive oxygen species by Mito Sox Red reagent. Mito Sox Red is a reagent from Invitrogen™ catalog #LSM360084
Figure 5:
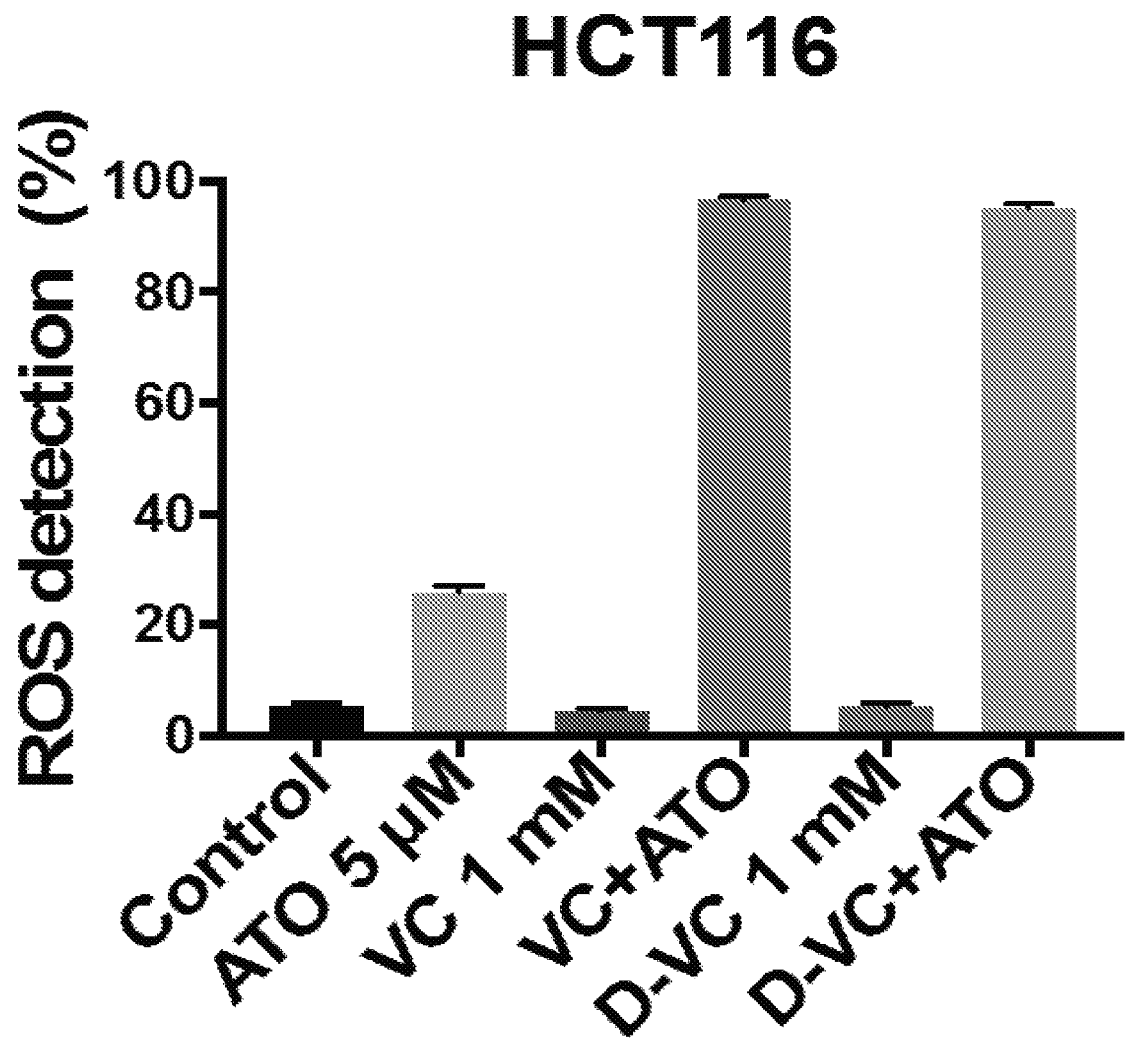
FIG. 5: Graphical representation of the presence of reactive oxygen species (ROS) as detected by flow cytometry. The ROS detection data shown in the FIG. 4 is presented as a graph.

It was anticipated that the cause of cytotoxic stress and apoptosis was the accumulation of reactive oxygen species (ROS), so HCT116 cells were treated as above and assayed for the presence of ROS by flow cytometry (FIG. 4). Similar to the cytotoxicity and apoptosis assays, treatment with vitamin C or its D enantiomer did not elicit an increase in ROS formation above baseline, and it was found that about 5% of cells were accumulating ROS (FIGS. 4 and 5). Treatment with 5 µM ATO increased the cells showing ROS accumulation to 26% (FIGS. 4 and 5). Treatment with vitamin C or D-vitamin C in addition to ATO increased ROS formation such that about 95% of cells were found to be accumulating ROS (FIGS. 4 and 5).

Example 2—In Vivo Xenograft Study of D-VC Treatment of KRAS Mutant Cancer

VC has been shown to work by competing with glucose. To avoid glucose fluctuations in blood, the food was withdrawn from mice 2 hrs prior drug injections and food was given back to mice after 2 hrs of the VC or D-VC injection.

Initially, the VC or D-VC (2 g/kg) were injected with ATO (8 mg/kg) at the same time. The injections for 2 weeks were not toxic for mice: body weight did not decrease). The tumor size did not show measurable change when measured by using the calipers.

To optimize the drug injections, a 2 hrs gap (time interval) between ATO and VC or D-VC injections was introduced. Following second injection, all mice (group of 5 mice) in the group of ATO+VC injections died and only 2 mice died from group of 5 of the ATO+D-Vitamin C injections. This indicated that introducing the 2 hr gap between injections caused a major toxic impact suggesting that the drug combination worked more effectively by introducing a oxidative stress in mouse tissues. It also suggests that D-VC is less toxic than VC in combination with ATO. The drug concentrations were decreased to avoid toxicity and it has been optimized for the mouse injections (VC or D-Vitamin C 1.5 g/kg and ATO 7 mg/kg). The optimized drug concentrations were effective in suppressing KRAS mutant tumor growth.

1.5 million human HCT116 (KRAS mutant) cancer cells were injected into nude mice, 5 mice per experimental group. After 10 days, and after when tumors reached at least 0.8 cm in size, mice were injected daily with either PBS, PBS+1.5 g/kg vitamin C, PBS+7 mg/kg ATO. PBS+7 mg/kg ATO+1.5 g/kg vitamin C, PBS+1.5 g/kg D-Vitamin C, or PBS+7 mg/kg ATO+1.5 g/kg D-Vitamin C. The mice were injected daily, 6 times per week, and rested one day per week, for a total of 15 total drug injections. Two days prior to the first injections with these concentrations, lower doses of the drugs were injected. Initially, ATO was injected at 3 mg/kg, while vitamin C or D-VC were injected at 1 g/kg. The following day, ATO was used at 7 mg/kg, while vitamin C and D-VC were used at 1 g/kg.

Figure 6:
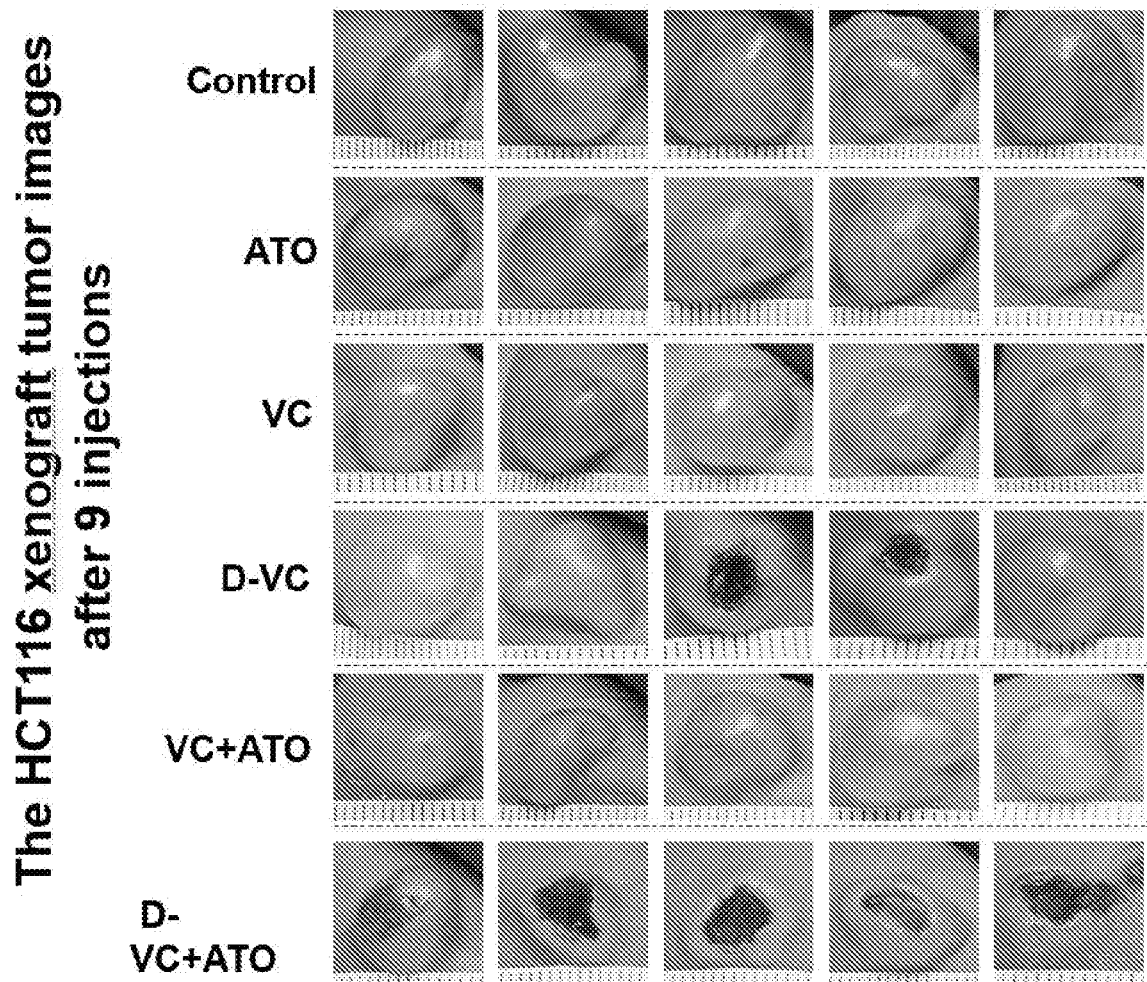
FIG. 6: HCT116 xenograft tumors after 9 injections. Pictured are the xenograft tumors of each of the 5 mice per treatment condition. Mice were injected intraperitoneally with PBS (control), Vitamin C (1.5 g/kg), D-Vitamin C (1.5 g/kg), ATO 7 mg/kg), ATO (7 mg/kg)+Vitamin C (1.5 g/kg) or ATO (7 mg/kg)+D-Vitamin C (1.5 g/kg). Mice were injected daily for 6 days and after $6^{th}$ injection mice were rested for one day. Scarring is observed in several tumors, including all of the D-VC+ATO treated tumors.
Figure 7:
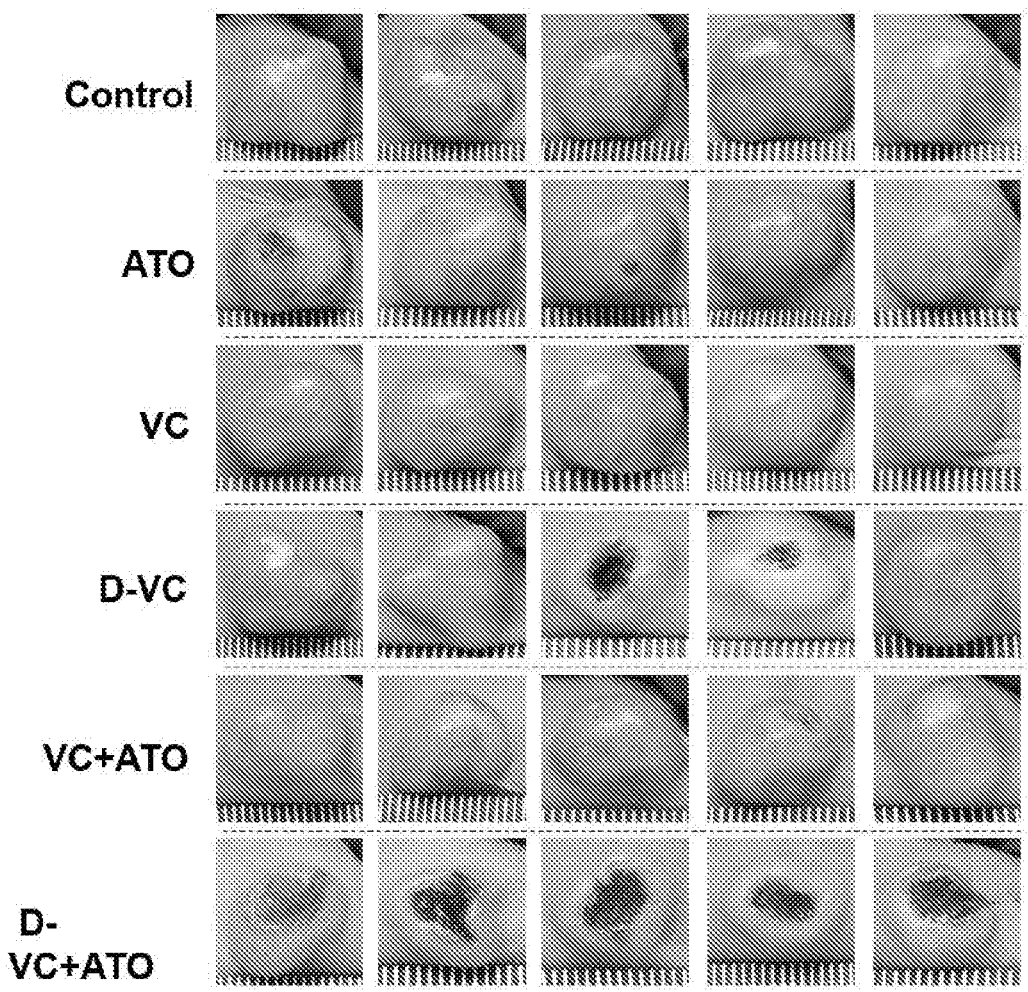
FIG. 7.

After 9 injections, the xenograft tumors were photographed (FIG. 6). Scarring was found on the tumors of D-VC (2/5 mice) and ATO+D-VC (5/5 mice) treated mice within the first week of injections (FIG. 6). After 12 injections, the tumors were imaged again (FIG. 7), Scarring was present in 2/5 ATO treated tumors, 2/5 D-VC treated mice, 1/5 of ATO and vitamin C treated mice, and all of the ATO plus D-VC treated mice (FIG. 7).

Figure 8:
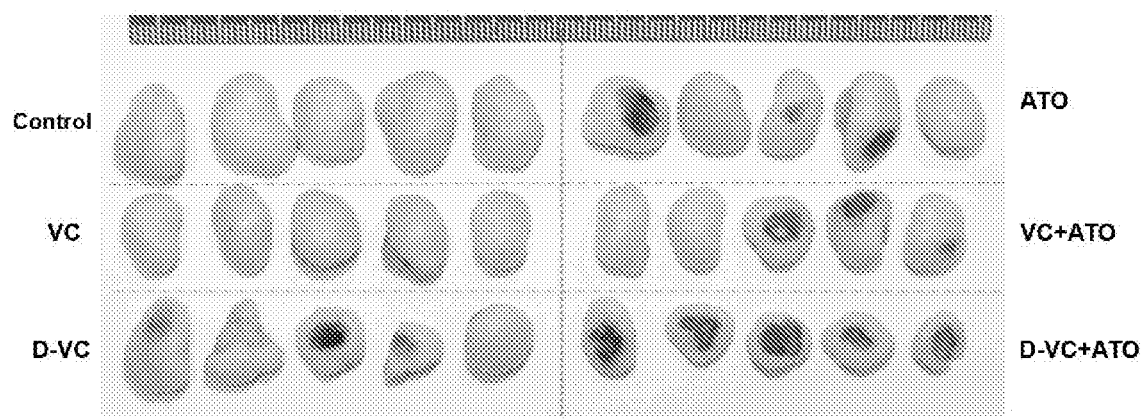
FIG. 8: HCT116 xenograft tumors after the $15^{th}$ (final) injection, following resection. The excised tumors are shown after 15 injections described in FIG. 6. Scarring is observed in several tumors, including all of the D-VC+ATO treated tumors.
Figure 9:
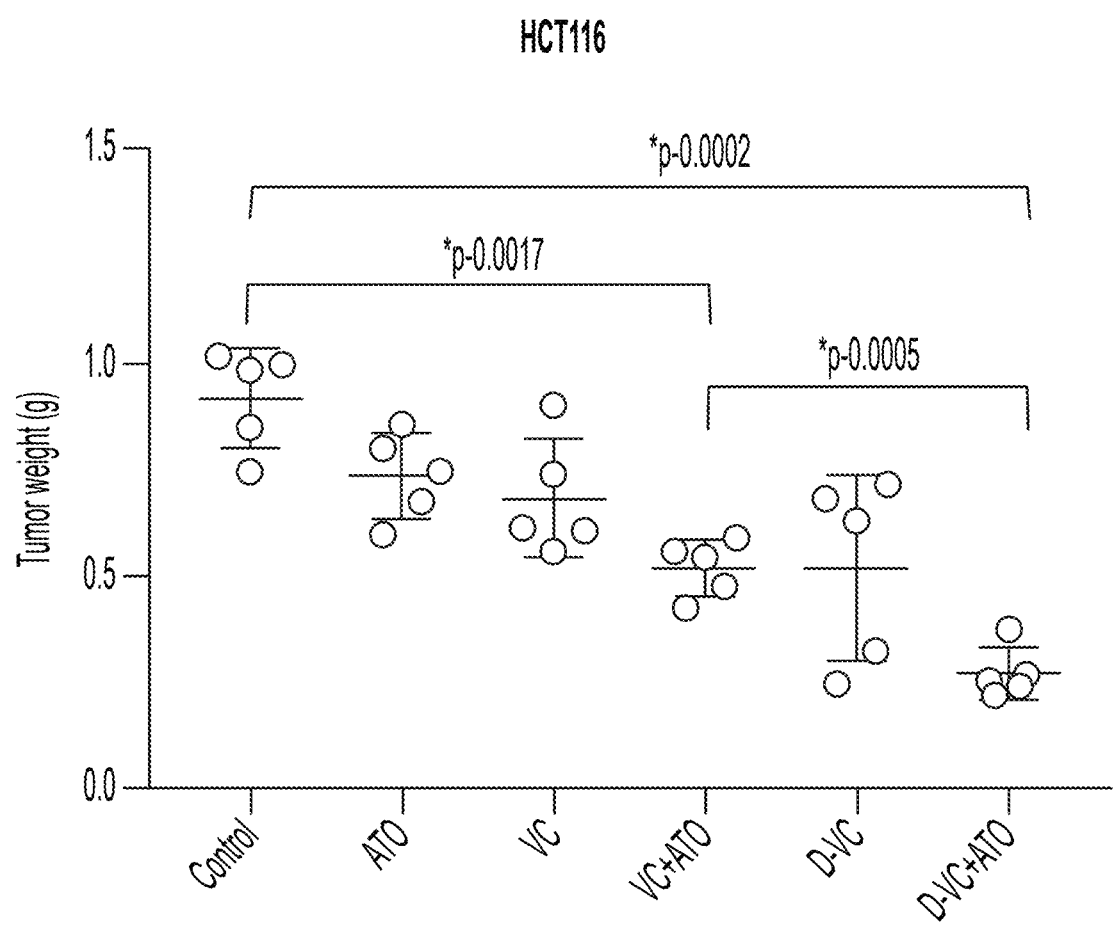
FIG. 9: Tumor weights following 15 injections. The p-values of the one way ANOVA statistical analysis shows a statistically significant difference in tumor weight between mouse groups shown in FIG. 8 treated with PBS vs VC+ATO, PBS vs D-VC+ATO, and VC+ATO vs D-VC+ATO.

The tumors were then isolated from the mice after the $15^{th}$ injection. The scarring observed as a result of the ATO plus D-VC treatment caused these tumors to have a "flat" appearance (FIG. 8). The initial scars were observed after 6 injections. The scars visible in other treatment groups generally appeared much later, and was less common than with ATO plus D-VC treatment. The tumors from each treatment group were then weighed (FIG. 9). The mean weights of the ATO, vitamin C, and D-VC treated tumors were lower compared to the PBS treated tumors, however these differences were not statistically significant (FIG. 9). Both the ATO plus vitamin C treated, and the ATO plus D-VC treated tumors weighed significantly less than the PBS treated tumors, and the D-VC plus ATO treated tumors weighed significantly less than the vitamin C plus ATO treated tumors (FIG. 9).

When compared to the PBS (control) injections, all components alone (ATO, vitamin C, or D-VC) show an inhibitory effect on tumor growth, and the D-VC treatment appeared to be more effective alone but its effect was not consistent (2 mice from group of 5). The combination treatments were found to be more effective than when the drugs were injected alone, as shown by the reduction in tumor weight. Importantly, the D-VC plus ATO combination was much more effective than the vitamin C plus ATO combination. Interestingly, it was also observed that the D-VC plus ATO treatment combination resulted in scarring or burning of tumors within 6 injections. The tumors in these mice became flat after 15 injections because of the scarring effect. The scarred tumors were observed in all 5 mice injected with the ATO and D-VC combination, whereas the scarring effect induced by the ATO plus vitamin C combination treatment was only observed after 15 injections and was only present in 3 of 5 samples.

Initial injections of the drug combinations showed only marginal impact on tumor growth, therefore the dose was increased as shown above. Second, the effect was enhanced when by introducing 2 hour gap (time interval) between ATO and D-VC injections. The injection scheme was ATO injection/2 hour gap/vitamin C or D-VC injection. It is likely that vitamin C or D-VC inactivate the oxidizing compound ATO in vivo, because both vitamin C and D-VC are known antioxidants. This inactivation, however, was only observed in the xenograft tumors, not in cell culture conditions. Further, it is also known that the effect of vitamin C treatment on KRAS mutant cancer cells is glucose dependent, To avoid glucose fluctuations in the blood and enhance the effect of vitamin C and D-VC, the drug injections were performed following withdrawal of the food from mice 2 hours prior ATO injections, and the food was only provided again 2 hours following the vitamin C or D-VC injections.

Accordingly, it has been found that the D configuration of VC (D-vitamin C or D-VC) is effective to induce oxidative stress in the KRAS mutant cancer cells. To strengthen the oxidative impact of D-VC on the KRAS mutant cells, D-VC was administered in combination with another oxidizing compound, Arsenic Trioxide (ATO). It was determined that the D-VC/ATO combination is highly cytotoxic to the KRAS mutant cancer cells of the human or mouse origin. This study also indicates that the D-VC/ATO combination application is more effective in suppressing KRAS mutant tumor growth in the mouse xenograft model than a combination of the L form of vitamin C (VC) and ATO. Therefore, the combination of D-VC and ATO can be used to treat KRAS mutant cancers. The KRAS mutations are common in pancreatic, colorectal, and lung cancers and there has been no effective intervention of the KRAS oncogene. The invention provided herein yields a potent cytotoxic combination to target mutant cancer cells, and particularly KRAS mutant cancer cells. The D-VC and ATO combination approach can be applied also to any type of cancer associated with a high expression of GLUT1 or cancers with a high glucose absorbance.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Linnen et al., *Mol Cancer Ther.*, 12(12):2792-2803, 2013.
Grad et al., *Blood*, 96(3):805-813, 2001.
Yedjou et al., *Arch Drug Info.*, 2:59-65, 2009.
Yun et al., *Science*, 350(6266): 1391-1396, 2015.

The invention claimed is:

1. A method for treating a KRAS mutant cancer comprising administering to a subject in need thereof a therapeutically effective dose of arsenic trioxide (ATO) and an optical isomer of L-vitamin C or pharmaceutically acceptable salts thereof, wherein the ATO and the optical isomer of L-vitamin C are administered in separate compositions, wherein the ATO and the optical isomer of L-vitamin C are administered within 24 hours of each other, and wherein the subject has been fasting at least 2 hours prior to the administration of ATO.

2. The method of claim 1, wherein the cancer exhibits elevated GLUT1 expression or a high glucose absorbance.

3. The method of claim 1, wherein the optical isomer of L-vitamin C is administered about 2 hours following ATO administration.

4. The method of claim 1, wherein the cancer is leukemia, colorectal cancer, pancreatic cancer or lung cancer.

5. The method of claim 4, wherein the leukemia is acute promyelocytic leukaemia (APL).

6. The method of claim 1, wherein the cancer is a pancreatic cancer, a colorectal cancer, or multiple myeloma.

7. The method of claim 1, wherein the cancer exhibits elevated GLUT1 expression.

8. The method of claim 1, wherein the method further comprises treatment with at least one other anti-cancer therapy.

* * * * *